US00PP30335P2

(12) United States Plant Patent
Klemm et al.

(10) Patent No.: US PP30,335 P2
(45) Date of Patent: Apr. 2, 2019

(54) ***PELARGONIUM* PLANT NAMED 'KLEPZ17484'**

(50) Latin Name: *Pelargonium zonale*
Varietal Denomination: KLEPZ17484

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/932,697

(22) Filed: Apr. 10, 2018

(51) Int. Cl.
*A01H 5/02* (2018.01)

(52) U.S. Cl.
USPC ..... Plt./330

(58) Field of Classification Search
USPC ..... Plt./263.1, 324, 325, 330
See application file for complete search history.

*Primary Examiner* — Susan McCormick Ewoldt
*Assistant Examiner* — Karen M Redden
(74) *Attorney, Agent, or Firm* — Barbara Campbell; Cochran Freund & Young LLC

(57) ABSTRACT

A new *pelargonium* plant particularly distinguished by large, red flowers on long peduncles and an upright, bushy, and round habit, is disclosed.

1 Drawing Sheet

Genus and species: *Pelargonium zonale*.
Variety denomination: 'KLEPZ17484'.

CROSS-REFERENCE TO RELATED APPLICATIONS

A Canada Plant Breeders Rights application was filed on Mar. 27, 2017, Application No. 17-9151; a Switzerland Plant Breeders Rights application was filed on May 24, 2017, Application No. 17-3148; and a European Community Plant Variety Office application was filed on May 31, 2017, File No. 2017-1451. 'KLEPZ17484' has not been sold or made publicly available more than one year prior to the filing date of the instant application.

BACKGROUND OF THE NEW PLANT

The present invention comprises a new and distinct variety of *pelargonium*, botanically known as *Pelargonium zonale* and hereinafter referred to by the variety name 'KLEPZ17484'. 'KLEPZ17484' originated from a cross-pollination in September 2012 in Stuttgart, Germany between the female *pelargonium* variety 'SIL Magnus' (unpatented) and the male *pelargonium* variety PAC Abelina 'Pacabel' (U.S. Plant Pat. No. 22,881).

Seeds from the cross-pollination were obtained. The seeds were sown and plants were grown for evaluation. A single plant was selected in June 2013 and subsequently named 'KLEPZ17484'. In August 2013 'KLEPZ17484' was first vegetatively propagated by vegetative cuttings. 'KLEPZ17484' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Large, red flowers on long peduncles; and
2. An upright, bushy, and round habit.

DESCRIPTION OF THE PHOTOGRAPH

This new *pelargonium* plant is illustrated by the accompanying photograph which shows an overall view of the plant. The photograph is of an approximately 8-9-week-old plant grown in Stuttgart, Germany under greenhouse conditions in May 2016. The colors shown are as true as can be reasonably obtained by conventional photographic procedures.

DESCRIPTION OF THE NEW VARIETY

The following detailed descriptions set forth the distinctive characteristics of 'KLEPZ17484'. The data which define these characteristics were collected from asexual reproductions carried out in Stuttgart, Germany. Data was collected on three-month-old plants in Stuttgart, Germany under greenhouse conditions in April 2017. Color references are to The R.H.S. Colour Chart of The Royal Horticultural Society of London (R.H.S.), 5$^{th}$ edition (2007).

Classification:
- *Family*.—Geraniaceae.
- *Botanical*.—*Pelargonium zonale*.
- *Common*.—*Pelargonium*.
- *Designation*.—'KLEPZ17484'.

Parentage:
- *Female parent*.—The female *pelargonium* variety 'SIL Magus' (unpatented).
- *Male parent*.—The male *pelargonium* variety PAC Abelina 'Pacabel' (U.S. Plant Pat. No. 22,881).

Plant:
- *Form*.—Bushy, round.
- *Habit*.—Upright.
- *Height*.—20.0 cm.
- *Spread*.—20.0 cm to 24.0 cm.
- *Natural flowering season*.—Spring to autumn.
- *Propagation type*.—Vegetative cuttings.
- *Time to produce a finished flowering plant*.—4 months.

*Time to initiate and develop roots.*—20 days.
*Root description.*—Fine and white.

Stems:
*Quantity of stems per plant.*—4 to 5.
*Color.*—RHS 177A.
*Surface texture.*—Moderately pubescent.
*Stem form.*—Round.
*Diameter.*—0.9 cm.
*Length.*—7.0 cm to 9.0 cm.
*Internode length.*—2.0 cm.
*Anthocyanin.*—RHS 176B.

Leaves:
*Arrangement.*—Alternate.
*Shape.*—Cordate.
*Apex.*—Obtuse.
*Base.*—Open.
*Margin.*—Crenate.
*Surface texture.*—Upper surface: Sparsely pubescent. Lower surface: Smooth.
*Length.*—6.0 cm to 7.0 cm.
*Width.*—7.0 cm to 9.0 cm.
*Color.*—Upper surface: RHS N137A and RHS N187. Lower surface: RHS N137A.
*Petiole.*—Length: 4.0 cm to 7.0 cm. Diameter: 0.3 cm. Color: RHS 187A. Strength: Medium.
*Venation pattern.*—Palmate.
*Venation color.*—Upper surface: RHS 187A. Lower surface: RHS 137D.

Inflorescence:
*Lastingness of flowers on the plant.*—8 to 12 days.
*Umbels.*—Quantity of umbels per plant: 2 to 3. Length: 8.0 cm. Diameter: 12.0 cm.
*Individual florets of the umbel.*—Quantity of florets per umbel: 8 to 14. Depth: 2.5 cm. Diameter: 5.0 cm.
*Fragrance.*—Absent.

Flower buds:
*Cluster shape.*—Round.
*Cluster size.*—Length: 4.0 cm. Width: 4.0 cm.
*Surface texture.*—Moderately pubescent.
*Bud.*—Height: 1.2 cm. Width: 0.6 cm. Shape: Elliptic. Apex: Acute. Base: Obtuse. Margin: Entire. Color: RHS 197B.

Petals:
*Quantity per flower.*—7 to 9.
*Shape.*—Drop-shaped.
*Apex.*—Entire.
*Base.*—Obtuse.
*Margin.*—Entire.
*Length.*—3.5 cm.
*Width.*—3.0 cm.
*Surface texture.*—Upper surface: Smooth. Lower surface: Smooth.
*Color of lobes.*—Upper lobes: Upper surface: RHS N57B. Lower surface: RHS N57A. Lower lobes: Upper surface: RHS N57B. Lower surface: RHS N57A.

Petaloids:
*Quantity per flower.*—1 to 3.
*Shape.*—Moderate.
*Apex.*—Moderate.
*Base.*—Obtuse.
*Margin.*—Entire.
*Texture* (*upper and lower surfaces*).—Smooth.
*Length.*—0.5 cm to 1.5 cm.
*Width.*—0.1 cm to 0.5 cm.
*Color.*—Upper surface: RHS N57B. Lower surface: RHS N57A.

Sepals:
*Number per flower.*—5.
*Shape.*—Elliptic.
*Apex.*—Acute.
*Base.*—Obtuse.
*Margin.*—Entire.
*Surface texture.*—Upper surface: Sparsely pubescent. Lower surface: Sparsely pubescent.
*Color.*—Upper surface: RHS 137D and RHS 187B. Lower surface: RHS 137D and RHS 187B.
*Length.*—1.2 cm.
*Width.*—0.3 cm.

Pedicel:
*Length.*—3.5 cm.
*Diameter.*—0.2 cm.
*Color.*—RHS 187A.
*Surface texture.*—Moderately pubescent.
*Strength.*—Medium.

Peduncle:
*Length.*—12.0 cm.
*Diameter.*—0.5 cm.
*Color.*—RHS 187B.
*Surface texture.*—Sparsely pubescent.
*Strength.*—Medium to strong.

Reproductive organs:
*Stamens.*—Quantity of stamens per flower: Moderate, 5. Anther length: 0.7. cm. Filament length: 0.8 cm. Filament color: RHS 45A. Pollen amount: Moderate. Pollen color: RHS 28A.
*Pistils.*—Number: 1. Stigma color: RHS 53B. Style length: 1.0 cm. Style color: RHS 53B. Ovary arrangement: Central. Ovary color: RHS 177B. Ovary diameter: 0.1 cm. Ovary length: 0.5 cm.

Fruit and seed set: None observed.
Disease and pest/insect resistance: None observed.

COMPARISON WITH PARENTAL LINES AND KNOWN VARIETY

'KLEPZ17484' is distinguished from its parents as described in Table 1:

TABLE 1

Comparison with Parental Lines

| Characteristic | 'KLEPZ17484' | Female parent 'SIL Magnus' | Male Parent PAC Abelina 'Pacabel' |
|---|---|---|---|
| Flower size | Large | Medium | Medium |
| Growth | Strong | Compact | Medium |

'KLEPZ17484' can be compared to the commercial variety 'SIL Bernd' (unpatented). Differences between the two varieties are described in Table 2:

TABLE 2

Comparison with Similar Variety

| Characteristic | 'KLEPZ17484' | Commercial line 'SIL Bernd' |
|---|---|---|
| Leaf color | Dark green | Medium green |
| Peduncle size | Long | Medium-short |
| Flower size | Large | Medium |

We claim:

1. A new and distinct variety of *pelargonium* plant named 'KLEPZ17484' as illustrated and described herein.

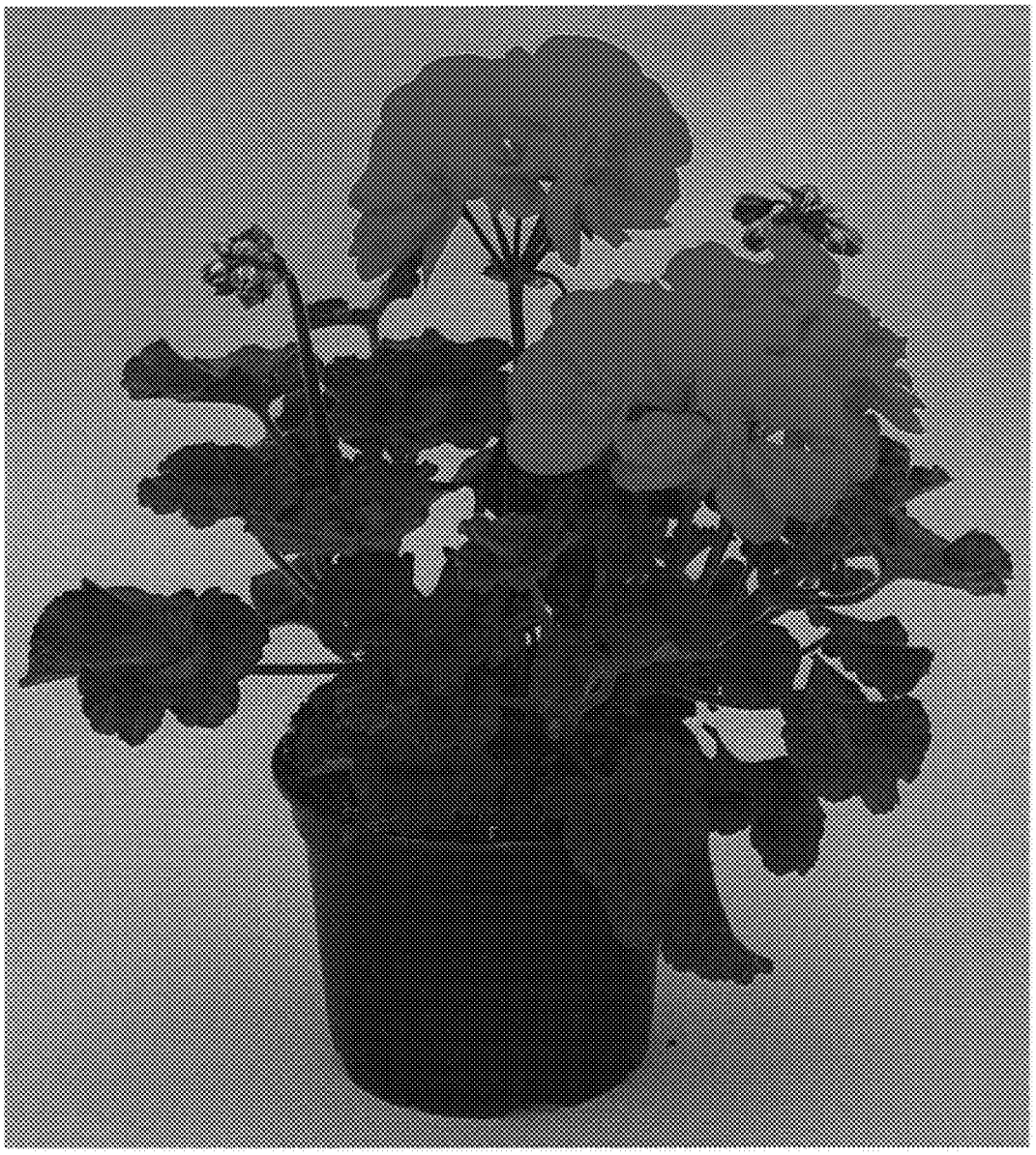

* * * * *